(12) United States Patent
Vlad et al.

(10) Patent No.: US 7,846,889 B2
(45) Date of Patent: Dec. 7, 2010

(54) SOLUBILIZING SYSTEMS FOR FLAVORS AND FRAGRANCES

(75) Inventors: Florin Joseph Vlad, Annandale, NJ (US); Rémy Mounier, Aulnay sur Mauldre (FR); Kenneth Wong, Geneva (CH); Aude Daugeron Jouault, Levallois-Perret (FR); Thomas Herd, Pompton Plains, NJ (US)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 12/643,269

(22) Filed: Dec. 21, 2009

(65) Prior Publication Data

US 2010/0098644 A1   Apr. 22, 2010

Related U.S. Application Data

(63) Continuation of application No. 11/689,635, filed on Mar. 22, 2007, now Pat. No. 7,655,613, which is a continuation of application No. PCT/IB2005/003329, filed on Oct. 19, 2005, application No. 12/643,269, which is a continuation of application No. 11/245,704, filed on Oct. 6, 2005, now abandoned, which is a continuation of application No. PCT/IB2004/001473, filed on Apr. 19, 2004, which is a continuation-in-part of application No. 10/421,216, filed on Apr. 21, 2003, now abandoned.

(60) Provisional application No. 60/620,557, filed on Oct. 20, 2004.

(30) Foreign Application Priority Data

Oct. 20, 2004   (EP) .................................. 04105185

(51) Int. Cl.
    *C11D 1/04*  (2006.01)
(52) U.S. Cl. ..................................................... 510/500
(58) Field of Classification Search .................. 510/500
    See application file for complete search history.

(56) References Cited

U.S. PATENT DOCUMENTS

| | | | |
|---|---|---|---|
| 4,285,973 A | 8/1981 | Edwards | 424/358 |
| 4,606,913 A | 8/1986 | Aronson et al. | 424/59 |
| 4,835,002 A | 5/1989 | Wolf et al. | 426/590 |
| 5,023,175 A * | 6/1991 | Hosoya et al. | 435/101 |
| 5,047,234 A | 9/1991 | Dickerson et al. | 424/76.2 |
| 5,079,227 A | 1/1992 | Handjani et al. | 512/2 |
| 5,108,643 A | 4/1992 | Loth et al. | 252/174.11 |
| 5,252,555 A | 10/1993 | Dartnell et al. | 512/4 |
| 5,283,056 A | 2/1994 | Chung et al. | 424/49 |
| 5,290,547 A | 3/1994 | Bilbrey | 424/76.6 |
| 5,374,614 A | 12/1994 | Behan et al. | 512/3 |
| 5,468,725 A | 11/1995 | Guenin et al. | 512/2 |
| 5,578,563 A | 11/1996 | Trinh et al. | 510/513 |
| 5,585,343 A | 12/1996 | McGee et al. | 512/1 |
| 5,798,111 A | 8/1998 | Kanga et al. | 424/401 |
| 6,316,545 B1 | 11/2001 | Sakuta | 524/837 |
| 6,403,109 B1 | 6/2002 | Stora | 424/401 |
| 6,703,034 B2 | 3/2004 | Parmar et al. | 424/405 |
| 6,766,817 B2 | 7/2004 | da Silva | 137/1 |
| 6,918,404 B2 | 7/2005 | Dias da Silva | 137/132 |
| 6,946,124 B2 | 9/2005 | Arnaud-Sebillotte et al. | 424/78.02 |
| 7,066,586 B2 | 6/2006 | da Silva | 347/85 |
| 7,655,613 B2 * | 2/2010 | Vlad et al. | 510/490 |
| 2001/0044392 A1 | 11/2001 | Trinh et al. | 510/101 |
| 2001/0051138 A1 | 12/2001 | Scafidi et al. | 424/66 |
| 2002/0187238 A1 | 12/2002 | Vlad | 426/590 |
| 2003/0146294 A1 | 8/2003 | Minamite et al. | 239/44 |
| 2004/0209795 A1 | 10/2004 | Vlad | 512/4 |

FOREIGN PATENT DOCUMENTS

| | | |
|---|---|---|
| EP | 0 316 726 A2 | 5/1989 |
| EP | 0 334 777 B1 | 9/1989 |
| EP | 0 571 677 A1 | 12/1993 |
| EP | 0 419 850 B1 | 1/1995 |
| EP | 0 631 771 B1 | 1/1995 |
| EP | 1 108 421 A2 | 6/2001 |
| EP | 1 243 185 A2 | 9/2002 |
| EP | 1 502 608 A2 | 2/2005 |
| WO | WO 89/08462 | 9/1989 |
| WO | WO 98/25651 | 6/1998 |
| WO | WO 98/26809 | 6/1998 |
| WO | WO 01/85121 A2 | 11/2001 |

(Continued)

OTHER PUBLICATIONS

Tokuoka et al., "Solubilization of Some Synthetic Perfumes by Anionic-Nonionic Mixed Surfactant Systems," J. Phys. Chem., 98:6167-6171 (1994).

(Continued)

*Primary Examiner*—John R Hardee
(74) *Attorney, Agent, or Firm*—Winston & Strawn LLP

(57) ABSTRACT

The present invention provides compositions and clear oil-in-water microemulsion containing up to 80% w/w of an oil, a surfactant system, a w/w oil/surfactant system ratio between 1 and 3, and a solubilizing-aid ingredient which is not a surfactant neither a VOC compound, the latter being present in an amount sufficient to ensure that the ratio oil/(surfactant+solubilizing aid) is comprised between 0.1 and 5. The present invention concerns also the articles and products associated the compositions and microemulsions, and the methods to manufacture them.

19 Claims, No Drawings

FOREIGN PATENT DOCUMENTS

| | | |
|---|---|---|
| WO | WO 01/88076 A1 | 11/2001 |
| WO | WO 02/34409 A2 | 5/2002 |
| WO | WO 02/068128 A2 | 9/2002 |
| WO | WO 2004/093836 A2 | 11/2004 |
| WO | WO 2004/110559 A1 | 12/2004 |
| WO | WO 2006/043177 A1 | 4/2006 |

OTHER PUBLICATIONS

International Search Report, application No. PCT/IB2004/001473, mailed Nov. 11, 2004.
Hydrophilic-lipophilic balance:http://en.wikipedia.org/wiki/Hydrophilic-lipophilic_balance , p. 1, Jun. 2009.
Pyrrolidone Carboxylic Acid PubChem: http://pubchem.nobi.nim.nih.gov/summary/summary.cgi?cid-499 , p. 1, Jun. 2009.

* cited by examiner

SOLUBILIZING SYSTEMS FOR FLAVORS AND FRAGRANCES

CROSS-REFERENCE TO RELATED APPLICATIONS

This application is (1) a continuation of application Ser. No. 11/689,635 filed Mar. 22, 2007 now U.S. Pat, No. 7,655,613, which is a continuation of International application PCT/IB2005/003329 filed Oct. 19, 2005, which claims the benefit of application No. 60/620,557 filed Oct. 20, 2004; and (2) a continuation of application Ser. No. 11/245,704 filed Oct. 6, 2005, now abandoned which is a continuation of International application PCT/IB2004/001473 filed Apr. 19, 2004, which is a continuation-in-part of application Ser. No. 10/421,216 filed Apr. 21, 2003, abandoned.

TECHNICAL FIELD

The present invention relates in particular to the flavor and fragrance industry and more precisely it provides compositions in the form of clear oil-in-water (o/w) microemulsions capable of carrying an oil of any composition and concentration.

The invention further relates to raw material concentrates that can be diluted with water to form the above microemulsions.

Other aspects of the invention concern the use of said microemulsions to perfume and flavor consumer articles, or to modify other attributes of such products such as texture, antibacterial properties, malodor coverage ability or yet nutritional or cosmaceutical properties. The products resulting from such use are also the object of the invention.

BACKGROUND ART

Generally speaking, water-based microemulsions containing perfumes or flavors, or yet other hydrophobic active materials, have already been reported in the prior art. Frequently, these prior known microemulsions, in order to provide proper dispersion of the oil in the water-based medium, contain large amounts of short chain alcohols, namely ethanol, or other VOC (Volatile Organic Compound) materials. In the flavor and fragrance field, however, there are advantages in resorting to the use of alternatives to these conventional microemulsions, in particular alternatives with low VOC content, which, although they dispense with the use of significant amounts of the latter, still retain all of the microemulsion's desirable aspects, such as sensorial performance, sprayability, diffusity, and skin feel, commonly associated with the presence of such short chain alcohols and in particular with ethanol.

By "VOC" we mean here the Volatile Organic Compounds as defined by the Environmental Protection Agency, and in particular we mean $C_1$-$C_5$ alkanols, such as ethanol, or $C_1$-$C_5$ alkanediols, such as ethylene glycol.

Low VOC microemulsions have also been reported in the prior art. However, generally, in formulating such microemulsions it is important to increase the total amount of surfactants so as to obviate the absence of VOCs, otherwise the final emulsions display a lack of clarity and/or stability problems, and this is unacceptable for the fragrance and flavor applications. The increase in the amount of surfactants in the final microemulsion typically results in products containing surfactant or tensoactive systems that are often in large excess with respect to the solubilized oil, namely the perfume or flavor. Obviously, a large excess of surfactant is also a disadvantage for such final products, in particular for perfumes or other products intended for application to the skin, hair or other surfaces such as textiles, wherein high surfactant content can lead to foamy, sticky, irritating or allergenic products that are unacceptable to consumers.

In this context, U.S. Pat. No. 5,374,614 provides a clear microemulsion for perfumery applications with a low VOC content and wherein the amount of surfactant used is reduced with regard to previously known similar microemulsions. The products there-described comprise less than 10% w/w of lower aliphatic alcohols and resort to the use of a surfactant mixture comprising at least 50% by weight of a primary non-ionic surfactant, relative to the total weight of surfactant mixture, together with a lower amount of ionic co-surfactant. Although these prior known microemulsions made it possible to provide products having a low content in aliphatic alcohols, they required careful selection of the surfactant system nature and concentration, as a function of the nature and concentration of the fragrance oil to be solubilized therein, to provide the desired clear microemulsion. As is described on column 6, lines 31 to 38 of this document, the perfume oil needed to be tested against a range of surfactants to allow selection of the surfactant possessing the right HLB value for each specific fragrance. In addition, we have been able to establish that, for certain types of fragrances, it was in fact impossible to obtain clear o/w microemulsions based on the teachings of U.S. Pat. No. 5,374,614. This is particularly true for fragrances containing large amounts of terpenes or musks for example. This is shown in the comparative examples presented further on.

Now, it is highly desirable in the perfume and flavor industry to be able to formulate clear o/w flavor and fragrance microemulsions of any flavor or fragrance composition, over large domains of concentrations, without having to significantly change the surfactant system. Moreover, it would be desirable to have available an unselective, or universal, solubilizing system, i.e., that, for any particular surfactant system and specific amount thereof, shows no significant dependency on the nature and concentration of the perfume in order to provide a microemulsion that remains clear and stable under storage conditions.

Moreover, as it follows from the above, it is also highly desirable to provide clear microemulsions that contain low amounts of surfactants and in particular surfactant amounts that are lower than the amount of solubilized oil.

The present invention provides unexpected and highly advantageous solutions to both these requirements.

The aim of the present invention is precisely to provide o/w microemulsions that, for any surfactant or surface active system, remain clear and stable upon concentration or dilution of the oil phase, in other words throughout the whole range of oil concentrations in the microemulsion that are useful in application. The invention therefore is not only an important improvement over the o/w microemulsions disclosed in U.S. Pat. No. 5,374,614, but is essentially universal, effective for any combination of oil and surfactant system that one desires to apply.

The presently described solution results from an unexpected interfacial synergistic effect between the surfactant system and a particular type of chemicals capable of enhancing the ability of any such surfactant system to solubilize any oil, namely perfume or flavor compositions, independently of the nature or concentration of the latter, and thus provide perfectly clear and stable microemulsions thereof, upon dilution in water.

SUMMARY OF THE INVENTION

We have now surprisingly discovered that the use of a suitable amount of an appropriate solubilizing-aid ingredient, in addition to the classical microemulsion ingredients disclosed for example in U.S. Pat. No. 5,374,614, i.e., a perfume, a surfactant system and water, can solve the problem cited above.

Therefore, the present invention relates to a composition comprising:
A) from 0.01 to 80% w/w of an oil;
B) a surfactant system in an amount such that the concentration ratio oil/surfactant is comprised between 1 and 3;
C) at least one solubilizing-aid ingredient selected from the group consisting of the ammonium, alkaline and alkaline earth salts of:
  i) a $C_5$-$C_{10}$ compound comprising an aromatic or non aromatic five or six member heterocyclic ring and one or two carboxylic functional groups;
  ii) a $C_2$-$C_7$ linear, branched or cyclic mono-, di- or tri-carboxylic acid;
  iii) benzoic, hydroxyl-benzoic or amino-benzoic acid, a $C_8$-$C_{12}$ benzoic, hydroxyl-benzoic or amino-benzoic acid substituted by one or two $C_1$-$C_5$ alkyl groups;
  iv) benzene-sulfonic acid, a $C_7$-$C_{11}$ benzene-sulfonic acid substituted by one or two $C_1$-$C_5$ alkyl groups, optionally hydroxylated naphthalene-sulfonic acid, an optionally hydroxylated $C_{11}$-$C_{16}$ naphthalene-sulfonic acid substituted by one or two $C_1$-$C_5$ alkyl groups;
  v) a halide, ascorbate, bicarbonate, thiocyanate; and
  vi) mixtures thereof;
D) optionally water;

and wherein the ratio between the amount of oil and the total amount of solubilizing system, the latter being formed of the surfactant system plus solubilizing-aid ingredient or ingredients, is comprised between 0.1 and 5.

According to a particular embodiment of the invention, there is provided a composition wherein the surfactant system is formed of a mixture of at least one non-ionic surfactant and one anionic surfactant.

DETAILED DESCRIPTION OF THE PREFERRED EMBODIMENTS

We have now surprisingly established that the compositions presently claimed are universal oil-solubilizing systems for the delivery or fragrance or flavor ingredients, or of other hydrophobic oils potentially useful to provide odor and/or taste to consumer products, and/or to modify the texture, nutritional, skin conditioning or other properties thereof.

The oil-solubilizing systems of the invention can in fact be diluted at will in substantially VOC-free media, preferably in water, provided that the conditions above are respected, to thus form a great variety of clear o/w microemulsions intended for use as, or in, consumer products.

According to advantageous embodiments of the invention, the compositions comprise a surfactant system containing one or more non-ionic surfactants and one or more anionic surfactants, the amount of anionic surfactant or surfactants being 50% or more of the total weight of the surfactant system. The relative amounts of anionic and non-ionic components of the surfactant system can however be varied at will, as a function of the desired end product to be obtained. Therefore, in other useful embodiments of the invention the non-ionic surfactant is present in a preponderant amount of the surfactant system, i.e. in an amount of at least 50% by weight.

Moreover, the invention also relates to compositions containing water, in the form of clear o/w microemulsions. The latter may contain large amounts of water, up to 80 or even 95% or more w/w, and will typically contain at least 10% of water.

In contrast to the classical micellar solubilization systems based on short- and/or medium-chain alcohols or non-ionic surfactants as co-surfactants, the specific solubilization systems of the invention above-mentioned can solubilize fragrances or flavor oils, at a variety of concentrations between 0.01% and up to 80% w/w, more preferably, for the microemulsions, of up to 20 or 30% w/w, without changing the surfactant system, unlike what was the case with the surfactant/co-surfactant systems disclosed in U.S. Pat. No. 5,374,614 for example, which were customized to the composition of the two specific fragrances disclosed therein, and to the fragrance concentration in the final products.

In the definitions above, and throughout the whole contents of the present disclosure, the abbreviation w/w represents weight to, or weight by, weight ratio, meaning the ratio between the weight of a specific ingredient and the weight of the clear composition or microemulsion.

Moreover, from heretofore, the ratio oil/(surfactant system+solubilizing-aid) shall be designated as the "O/(S+SA)" ratio, O standing for the oil, more particularly the hydrophobic perfume or flavor, or other similar ingredient having malodor counteracting, texture modifying and/or nutritional, nutraceutical or cosmaceutical utility, S standing for the surfactant system and SA for the solubilizing-aid ingredient or ingredients of the invention.

By "surfactant" or "surfactant system" it is meant here the ensemble of ingredients that serve to solubilize the oil and prepare clear microemulsions thereof in water and which are not part of the solubilizing-aid ingredient as defined above.

By "microemulsion" we mean here a thermodynamically stable one-phase optically isotropic system that forms spontaneously, with no need to apply any substantial external force, and which is clear at a temperature comprised between 0° and 80° C., more preferably between 3 and 80° C.

By "clear" micro emulsions we mean here microemulsions which are clear throughout the desired range of oil concentrations, i.e. which present a clarity preferably comprised between 0 and 90 NTU, when measured between 400 and 600 nm in a 2.5 cm cell at 25 C.

By "clarity" we mean here the measure of the light scattered, at an angle of 90°, by the invention's microemulsion.

According to a praised embodiment of the invention, the microemulsion has clarity comprised between 0 and 50 NTU when measured in the same conditions as specified above.

In more particular embodiments of the invention, a specific range of surface tension can also characterize the invention's microemulsion. Thus, specific microemulsions have a surface tension, measured at 25° C., not above 30 mN/m, more preferably comprised between 20 and 30 mN/m, even more preferably comprised between 23 and 28 mN/m. Therefore, said microemulsions can contain large amounts of low polar oils.

The possibility to have crystal clear low VOC or VOC-free microemulsions containing large amounts of low polar oils is an unexpected result. Indeed, a person skilled in the art knows that it is particularly difficult to dissolve low polar oils in water, especially in large amounts, without the substantial use of VOCs or of oil/surfactant ratios largely below 1.

By "low VOC" or "VOC-free" microemulsions it is meant here microemulsions wherein the medium used to solubilize the oil, i.e. the surfactant system, the solubilizing-aid and the water, have not been added of any volatile organic compounds (VOC), namely of solvents such as ethanol, isopropanol or other $C_1$ to $C_5$ alkanols.

As mentioned above, when incorporated in water, the invention's solubilizing systems provide clear microemulsions which also display very good stability, e.g. phase separation is not observed within a reasonable frame of time. Indeed, the invention's microemulsions are commonly stable for at least 30 days, at temperatures comprised between 3° and 60° C. Furthermore, in some cases, nearly thermodynamic stability, e.g. more than 6 months at temperatures comprised between 2° and 45° C., was achieved.

The range of temperatures in which the invention's microemulsion shows very good stability is a function of the amount, as well as the exact nature, of the oil, surfactant system and solubilizing-aid ingredient used. Therefore in some cases it is possible that the stability temperature range of the named microemulsions is narrower, e.g. from 5° to 45° C. only, or wider, e.g. from 0° to 80° C.

By "oil" we mean here a lipophilic organic liquid that is essentially insoluble in water. An example of a suitable oil is a liquid that comprises at least 75% w/w, or even 90% w/w or more, of a flavor or a perfume, or of a flavor or perfuming composition. Said oil may also consist of a flavor or a perfume. For any particular surfactant system selected, the nature of the fragrance or flavor oil to be solubilized is however immaterial for the purpose of the invention, the person skilled in the art being able to choose a solubilizing-aid ingredient amongst those above-mentioned which is suitable to provide compositions and clear o/w microemulsions having the appropriate amount of perfume or flavor.

Embodiments of the microemulsions of the invention which are particularly useful for perfumery, namely to prepare fragrances to be sprayed or otherwise applied on the skin, may contain 60% w/w or more of water, and an amount of solubilized oil, namely perfume, comprised between 0.1 and 30% w/w, more preferably between 5 and 20% w/w, even more preferably between 5 and 15% w/w.

According to advantageous embodiments of the present invention, particular useful in perfumery, the composition may be a clear o/w microemulsion, comprising from 5 to 15% w/w of solubilized perfume and an amount of water between 75% and 85% by weight, relative to the weight of the microemulsion.

Even very hydrophobic oils such as fragrances, flavors, or ingredients thereof, that contain only small amounts of polar solvents, or are completely free of polar solvents, can be solubilized in the form of stable compositions and clear microemulsion products. Any perfuming composition that contains for example from 5% w/w to 99% w/w of terpenes, and/or from 5 to 30% w/w of musks, relative to the total amount of the oil, can thus be solubilized. Said terpenes may be of wood or citrus origin, such as terpineol, or d-limonene. Non-restrictive examples of musks include in particular the macrocyclic ketones and lactones such as pentadecanolide, hexadecanolide, HABANOLIDE® (11,12-pentadecenolide; origin: Firmenich SA), but also other musky odor materials commonly know to be difficult to solubilize in water-based compositions. These are surprising results, it being well-known that such perfumes are particularly difficult to solubilize in the form of VOC-free microemulsions.

Moreover, as the perfume or perfuming composition there can be used any perfuming ingredient or, as happens more often, any mixture of perfuming ingredients currently used in perfumery, e.g. of compounds capable of imparting an olfactive effect to the composition to which they are added, to impart thereto a desired odor or to modify its odor. Likewise as regards flavors or flavor compositions, which are ingredients, or mixtures of ingredients able to impart or modify the taste and texture characteristics of foodstuffs, beverages, edible pharmaceuticals and other edible consumer products. Said perfuming or flavoring ingredients can be of natural or synthetic origin. A detailed description of said ingredients would not be warranted here and, in any case, it cannot be exhaustive. Generally speaking, it can be mentioned that these ingredients belong to chemical classes as varied as alcohols, aldehydes, ketones, esters, ethers, acetates, nitriles, terpene hydrocarbons, nitrogenous or sulphurous heterocyclic compounds and essential oils of natural or synthetic origin. The nature of these ingredients can be found in specialized books of perfumery and flavor ingredients, e.g. in S. Arctander (Perfume and Flavor Chemicals, Montclair N.J., USA 1969), or similar textbooks of reference, and a more detailed description thereof is not warranted here. The selection of such ingredients is carried out by the perfumer or flavorist without particular difficulty, on the basis of her/his general knowledge and as a function of the nature of the product to be modified and of the desired sensory effect, i.e. the perfuming or taste effect that is to be imparted to the consumer product to be perfumed or flavored.

The oil may also contain a suitable solvent, in a quantity of up to 40% w/w of the oil, but preferably of up to 25% w/w of the oil. Current such solvents in perfumes and flavors include triacetin and dipropylene glycol, as well as diethyl phthalate. The presence of a solvent which is not a VOC may be useful to obtain a monophasic oil or to modulate the surface tension of said oil. As examples of suitable solvents, one may cite polar or non-polar low molecular weight solvents such as isoparaffins, paraffins, hydrocarbons, silicon oils, perfluorinated aliphatic ethers, glycol ethers, glycol ether esters, esters, or ketones. Non-restrictive examples of such solvents include dimethicone or cyclomethicone, which are commercialized by Chemsil Silicon INC. under the trade names COSMETIC FLUID® 1288, and respectively COSMETIC FLUID® 1387, jojoba oil, perfluoroisobutyl methyl ether, diethyl phthalate and isopropyl myristate.

Solvents that are currently used in flavors include dipropylene glycol, ethanol and triacetin.

Other possible ingredients of the oil are fixatives or ingredients able to impart nutritional and health properties to the consumer products. Examples of the latter are fish oil and other desirable fats known for their health improving properties, vitamins, cosmetic agents, skin conditioning and sun screening agents, etc. The oil composition may also contain antibacterial agents or malodor counteracting agents.

Concerning the physical properties of the oil, one can use a large variety of oils. According to particular embodiments of the invention, the fragrance or flavor oil has a surface tension comprised in a specific range namely comprised between 20 and 50 mN/m, at 25° C., more preferably between 28 and 35 mN/m. It is also possible to use as oil a low polar oil, in particular a low polar perfume. By "low polar oil or perfume" we mean here, for example, an oil or perfume rich in highly hydrophobic ingredients or an oil or perfume that contains only small amounts of polar solvents or is completely free of polar solvents.

As low polar perfumes one can mention those containing from 5% w/w, or even 20% w/w, to 99% w/w of terpenes and/or from 5 to 30% w/w of musks; percentages being relative to the weight of the oil.

As mentioned above, the oil may represent between 0.01 and 80% of the composition's total weight. According to particular embodiments of clear microemulsions following the invention, the perfume content represents preferably from 0.1 to 15 or 20% w/w, or even 30% w/w of the microemulsion. Very typical and preferred embodiments contain 5 to 15% w/w of solubilized perfume in the form of clear o/w microemulsions.

Flavor compositions will typically contain lower amounts of oil, as low as 0.05% or even 0.01% w/w, particularly when in the form of clear beverages.

Concentrated perfume compositions can typically contain 40%-60% or even up to 70% or 80% w/w of perfume oil.

The surfactant system, which is one of the mandatory elements of the invention's compositions, may be advantageously described as consisting in an anionic fraction, and a non-ionic fraction. The anionic fraction may contain a single anionic surfactant or a mixture of anionic surfactants.

Suitable anionic surfactants comprise the salts of $C_6$-$C_{24}$ mono- or di-sulfonic, alkylsulfuric, alkylarylsulfuric, alkylarylphosphate or carboxylic acids and also the polyethylene glycol co-polymers with sulfonic or carboxylic acids. Specific, but not limiting examples of said anionic surfactants are sodium, potassium, ammonium or mono-, di- or tri-ethanolammonium salts of $C_6$-$C_{12}$ dialkyl sulfosuccinic acids (such as sodium dioctyl-sulfosuccinate), $C_7$-$C_{24}$ alkarylsulfonic acids (such as sodium dodecyl benzenesulfonate), $C_6$-$C_{15}$ alkylsulfuric acid (such as sodium dodecylsulfate), $C_{10}$-$C_{20}$ acyl glutamic acid (such as disodium cocoyl glutamate or polyethylene glycol/dimethicone sulfosuccinic acids (such as disodium PEG-12 dimethicone sulfosuccinate known under the trade name MACKANATE® DC-50 from the McIntyre Group).

The non-ionic fraction may contain a single non-ionic surfactant or, according to other embodiments of the invention, a mixture of non-ionic surfactants. In particular embodiments of the invention the non-ionic surfactant will have a HLB value comprised between 9 and 18, although non-ionic surfactants having a HLB outside this range may be used.

Suitable examples of said surfactants include ethoxylated and/or propoxylated ($C_5$-$C_{12}$ alkyl)phenols ethers containing 5 to 20 EO or PO units (such as polyethylene glycol nonylphenyl ethers, polyethylene glycol octylphenyl ethers, also known under the generic tradename) POLYSTEP®, polyethylene glycol sorbitol ether containing 3 to 30 EO units (such as sorbitol esters with oleic, myristic, stearic, palmitic acid, known under the tradenames TWEEN® from ICI or GLYCOSPERSE® from LONZA), sucrose esters with $C_8$-$C_{20}$ fatty acid (such as sucrose esters with oleic, palmitic or stearic acid, such as Ryoto Sugar Ester M-1695 commercialized by Mitsubishi-Kagaku Foods Corporation), ethoxylated aliphatic $C_6$-$C_{20}$ alcohols containing 2 to 30 EO units (such as ethoxylated secondary $C_6$-$C_{20}$ alcohols), $C_8$-$C_{20}$ polyglyceryl esters (such as glycerol-polyethylene glycol oxystearate commercialized by BASF under the trade name CREMOPHOR® CO40), polyethylene glycol and polypropylene glycol block copolymers (such as those known under the tradename PLURONIC® from BASF), ethoxylated glycol ether containing 2 to 30 EO units (such as PEG-10 stearyl ether also known under the trade name VOLPO® S-10 from CRODA), or polyethylene glycol mono- or diester of aliphatic $C_5$-$C_{11}$ carboxylic acids containing 2 to 10 EO units (EO stands for ethylene oxide and PO stands for propylene oxide).

Other surfactant systems which are suitable for use according to the invention, as shown in the examples presented further on, include the systems cited for example in U.S. Pat. No. 5,374,614, the contents of which are hereby included by reference.

The resulting water-based surfactant systems have a surface tension value of less than 32 mN/m, more preferably between 22 and 28 mN/m, even more preferably between 23 and 26 mN/m.

In all embodiments of the invention the amount of surfactant system used to obtain a composition or a clear microemulsion according to the invention is kept to as low a value as possible in order to avoid the above-cited ill-effects associated with large contents of surfactant. Moreover, for any particular fragrance or flavor oil, the weight ratio (oil/surfactant system) in the microemulsion can be kept constant for all concentrations of oil, namely perfume or flavor, meaning that it can be kept independent from the amount of oil that one wants to solubilize, provided that the appropriate solubilizing-aid and amount are used.

In fact, the presence of the solubilizing-aid ingredient in the microemulsions according to the invention makes it possible to vary the concentration of perfume or flavor in the microemulsion, as well as the amount of water in the water phase thereof, without touching the oil/surfactant ratio, and this for any type of fragrance or flavor in any specific surfactant medium, by varying the solubilizing-aid concentration and nature as a function of the oil to be solubilized and the desired amount of oil.

In a general manner, the solubilizing-aid ingredient or mixture of ingredients is used in amounts such that the ratio O/(S+SA) is comprised between 0.1 and 5, for an oil/surfactant system ratio comprised between 1 and 3. Preferred compositions and clear microemulsions according to the invention display an oil/surfactant ratio above 1.0, preferably between 1.0 or 1.2 and 2, the ratio O/(S+SA) being preferably comprised between 0.5 and 2.

By the expression "solubilizing-aid ingredient" we mean here an organic or inorganic salt, or a precursor thereof, of low molecular mass, e.g. below 400 g/mol. As solubilizing-aid ingredient it can also be used a mixture of said salts.

Said compounds, which per their nature are neither surfactants nor solvents or solubilizers, have been found to improve the solubility of organic compounds in water. In fact, and unexpectedly, these salts, and their acid precursors, are able to enhance the oil-solubilization capacity of the surfactant system. In other words, in the presence of a solubilizing-aid ingredient, as defined above or below, the same amount of surfactant is able to solubilize in the water phase more oil than if the solubilizing-aid ingredient was not present. In addition, for any particular surfactant system, we have unexpectedly established that it will always be possible to solubilize a fragrance or flavor composition and to obtain a perfectly clear o/w microemulsion thereof, provided that the above-defined conditions of the invention are met.

The clarity of the microemulsion thus obtained is significantly and unexpectedly improved by the presence of the solubilizing-aid ingredient.

Thus, the presence of at least one of the above-mentioned salts has been found to be essential in order to ensure an oil/surfactant system ratio of at least 1, as well as a crystal-clear appearance, i.e. a high clarity or, if preferred, a low turbidity of the microemulsions according to the invention.

According to a particular embodiment of the invention, suitable salts are selected from the group consisting of sodium, potassium, magnesium and calcium salts of pyridine carboxylic acids, proline acid, pyrrolidone carboxylic acid, benzoic acid, hydroxyl-benzoic acid, amino-benzoic acid, lactic acid, ascorbic acid, bicarbonate, succinic acid, oxalic acid, tartaric acid, citric acid, a $C_8$-$C_{10}$ derivative of benzoic, hydroxyl-benzoic or amino-benzoic acid substituted by one or two $C_1$-$C_3$ alkyl groups (such as the sodium salt of p-methyl-benzoic acid or of p-isopropyl-hydroxyl-benzoic acid), benzene-sulfonic acid, a $C_7$-$C_9$ benzene-sulfonic acid substituted by one or two methyl or ethyl groups (such as potassium toluene sulfonate), optionally hydroxylated naphthalene-sulfonic acid, an optionally hydroxylated $C_{11}$-$C_{16}$ naphthalene-sulfonic acid substituted by one or two $C_1$-$C_5$ alkyl groups (such as sodium butylnaphtalene sulfonate), $C_3$ to $C_6$ alkanoic acids (such as the sodium salt of pentanoic acid), and any mixture of said salts.

In particular, the solubilizing-aid ingredient may be advantageously chosen amongst the following compounds: pyrrolidone carboxylic acid sodium salt (also known as AJIDEW® NL-50 from Ajinomoto), sodium benzoate, sodium L-lactate, calcium L-ascorbate, sodium bicarbonate and di-sodium succinate, and mixtures thereof.

As mentioned above, the solubilizing-aid ingredient is present in an amount such that the microemulsions according to the invention are clear.

The amount of solubilizing-aid to obtain a clear microemulsion according to the invention depends on the exact nature of the oil, on the surfactant mixture, and on the amount of oil present. The person skilled in the art is able to thus adjust the necessary amount of solubilizing-aid to obtain the desired clear microemulsions, provided that the O/S and O/(S+SA) ratios are within the ranges defined above.

Concerning the fourth component of the microemulsion, i.e. water, it is useful to mention that it is preferable to use de-ionized water. The quality of water used is such that it has no substantial content in salts that might interfere with the formation of clear microemulsions.

The invention's compositions and microemulsions can also comprise, as optional components, one or more ingredients such as colorants, anti-microbial or antibacterial agents, malodor counteracting agents, antioxidants, preservatives, chelating agents or UV-inhibitors and skin conditioning agents. Such types of materials are well known to a person skilled in the art and do not need a more detailed description. Whenever said ingredients are added to the microemulsion, they will typically represent no more than 10% w/w, more preferably 3% w/w, or even 2% w/w, the percentages being relative to the total weight of the composition or micro emulsion.

The invention's microemulsions can be prepared according to any method known in the art. A suitable method consists in dissolving into the water the surfactant system, to form a clear micellar solution which acts as a pre-microemulsion. Possibly, during this stirring stage a nitrogen blanket may be useful to avoid foaming and to protect the system from oxygen contamination. To the resulting clear micellar solution is added under gentle stirring the fragrance or flavor oil such that a milky emulsion results. Finally the latter is turned into an isotropic clear, single-phase product by addition of the solubilizing-aid ingredient, and whenever necessary the optional ingredients to form a clear microemulsion.

According to another suitable method, one can proceed by dissolving into the water the surfactant system, to form a clear micellar solution. To the resulting micellar solution are added under gentle stirring the solubilizing-aid ingredient and, whenever necessary, the optional ingredients to form an initial oil-free microemulsion. Under gentle mixing the resulting oil-free composition can easily solubilize the corresponding amount of oil, namely a perfume or flavor, to form an isotropic clear, single-phase microemulsion product.

High mechanical forces such as shear forces are not necessary to manufacture the present microemulsions. Usually a clear product is obtained in a short time, less than 30 min stirring, and sometimes even instantly upon admixture of the ingredients.

These methods also make it possible to obtain the microemulsions starting from products presented in the form of separate ingredient kits to be admixed at a later stage by the user. In particular, it goes without saying that the compositions of the invention do not require water to be pre-added to the other ingredients before use of the composition by the consumer or by a consumer product manufacturer.

The ingredients, to with the surfactants, the solubilizing-aid ingredient or ingredients and the oil, may all be provided separately and admixed in-situ by the user, for example at a manufacturer's plant anywhere in the World, or by the consumer, the water being locally provided. For example, if a single dosage formulation is contemplated for direct use by a consumer, it is possible to provide the ingredients in concentrated form, together with instructions for dilution in water by the consumer upon usage of the single dose of concentrated solubilizing system. The latter is already in the form of an oil concentrate or in the form of an oil-free composition intended to be admixed with the oil provided in a separate oil package.

Separate pre-admixed mixtures of ingredients may therefore be prepared and commercialized for final admixture at a manufacturing plant or local use site. Thus, the surfactants and solubilizers other than the solubilizing-aid ingredient may be admixed together to form the surfactant system (S) composed of non-ionic and anionic surfactants, and the solubilizing-aid (SA) ingredient (or mixture of ingredients) added thereto to prepare a complete solubilizing system. The latter can then be added of fragrance and water in the appropriate concentrations. Such solubilizing systems are also embodiments of the present invention, as they constitute starting raw material ingredients for the preparation of the oil-containing compositions and microemulsions according to the invention.

The solubilized oil concentrates, formed of a solubilizing system as hereabove and the oil, in particular the fragrance or flavor oil, are compositions according to the invention, which make it possible to obtain clear microemulsions upon dilution in water. Such concentrated compositions shall typically contain oil amounts, in particular fragrance or flavor amounts, forming up to 40-60%, or even 70% or 80% by weight of the concentrate, wherein the ratio between the oil and the surfactant system S is comprised between 1 and 3 and the ratio between the amount of oil and that of the overall solubilizing system, i.e. the surfactant system S plus the solubilizing-aid SA, is comprised between 0.1 and 5, more preferably between 0.5 and 2.

All these compositions, as well as the o/w microemulsions resulting from their incorporation in water, are objects of the invention as here-disclosed. They may constitute components for the delivery of perfume or flavor in consumer products, or they may assume themselves the form of a consumer product, in particular of a perfume or cologne, a body spray or other body or hair perfuming product, an ironing water or a textile spray, an all-purpose cleaner (APC) or a cosmetic composition. The invention also relates to such consumer products.

Typical food products wherein the microemulsions can be used include beverages, creams, dairy products and salad sauces.

Moreover, it is clear that pre-microemulsion compositions containing water and the surfactant system can be provided and commercialized separately from the oil, respectively the solubilizing-aid ingredient, or even from mixtures of the latter with the oil. Alternatively, an oil-free pre-microemulsion containing the surfactant and solubilizing agent can be provided separately from the oil to be solubilized. The water can be added separately in-situ, upon manufacture of the desired microemulsion products, or upon use of single dosage products by the consumer.

The above-mentioned oil-free products and pre-microemulsions are therefore excellent solubilizing media which allow to obtain highly clear microemulsions containing an oil such as a perfume or flavor.

The compositions according to the invention can thus be concentrated or diluted, i.e. they may contain large amounts of water or, on the contrary large amounts of perfume or flavor and even no water. The concentrated solubilizing systems, i.e. the oil-free or oil containing compositions that contain substantially no water or water contents not above 10% w/w, and microemulsions according to the invention, shall comprise amounts of surfactant system, solubilizing-aid and, as the case may be, oil in such relative proportions that the ratio oil/surfactant (O/S) is comprised between 1 and 3, preferably between 1.0 and 2, and the ratio O/(S+SA) is comprised between 0.1 and 5, preferably between 0.5 and 2.

The compositions and in particular the clear microemulsions of the invention may be used as such, in particular as carriers of fragrance for topical application on the skin, hair or other surfaces such as tiles, glass or textiles. They are particularly useful as textile fresheners, for covering textile malodor, on clothes, carpets and curtains for example. Likewise, they can be used as all-purpose-cleaners to deodorize and perfume tiles, windows, kitchen and bathroom surfaces, etc. They may also be useful for perfuming clothes during ironing, thus in the form of ironing waters.

A suitable consumer article comprises a microemulsion as described above together with a suitable container and optionally a means to produce an aerosol, if a spray type product is desired. Non-limiting examples of such consumer articles are fine fragrance compositions, deodorants and fresheners, as well as hair or skin preparations, such as fine perfumery articles, textile sprays, cosmetics and similar.

In another embodiment, said consumer articles comprise a microemulsion according to the invention and a consumer product base. For the sake of clarity, it has to be mentioned that, by "consumer product base" we mean here a consumer product which is compatible with perfuming or flavoring ingredients in particular. In other words, a perfumed article according to the invention comprises the functional formulation, as well as optionally additional benefit agents, corresponding to a consumer product, e.g. a detergent or textile freshener, and an olfactive effective amount of at least one of the invention's microemulsions. Thus a suitable consumer product base is, for example, a surface cleaning product, a hygiene product, a hair care product such as a shampoo, a body-care product, a cosmetic preparation, a fabric refresher, an ironing water or a wipe.

The nature and type of the constituents of the consumer product do not warrant a more detailed description here, which in any case would not be exhaustive, the skilled person being able to select them on the basis of its general knowledge and according to the nature and the desired effect of said product.

In all these consumer products the amount of composition or microemulsion according to the invention that is incorporated in the product is such as to deliver in the latter a concentration in active oil ingredient that is preferably of between 0.01 and 30% weight, relative to the weight of product, but may be much higher if a concentrated oil product is desired.

A further object of the present invention is the use of a composition or microemulsion according to the invention as a perfuming or flavoring ingredient, for the delivery of a nutritional supplement, an antibacterial agent, a malodor counteracting composition or yet a skin conditioning or a sun screen agent. In other words, a method to confer, enhance, improve or modify the odor, flavor, nutritional, texture, antibacterial, malodor counteracting and/or sun-screening properties, or skin-conditioning benefits, of a composition or of an article, which method comprises adding to said composition or article an effective amount of a composition or microemulsion as defined above, to obtain the desired effect.

EXAMPLES

The invention will now be described in further detail by way of the following examples.

Example 1

Preparation of Perfume-in Water Microemulsion According to the Invention

A perfume having a high content in terpenes was obtained by admixing the following ingredients:

| Ingredients | Parts by weight |
| --- | --- |
| Citronellyl acetate | 3 |
| Geranyl acetate | 9 |
| Linalyl acetate | 276 |
| 10% * Aldehyde C10 | 3 |
| 10% * Aldehyde C12 | 12 |
| Methyl anthranilate | 16 |
| Bergamote essential oil | 226 |
| Cetalox ® [1] | 5 |
| Lemon essential oil | 318 |
| Dihydromyrcenol [2] | 60 |
| Dipropylene glycol | 20 |
| 10% * Elemi [3] | 20 |
| Fleuria 41063 B [4] | 3 |
| Ethyl linalol | 66 |
| 10% * 3-(4-Methoxyphenyl)-2-methylpropanal [4] | 30 |
| Geraniol | 6 |
| 50% * Habanolide ® [5] | 130 |
| Hedione ® [6] | 215 |
| Hedione ® HC [7] | 72 |
| 10% ** Indol | 12 |
| Iso E super [8] | 85 |
| Lavandin grosso essential oil | 26 |
| 1% * Liffarome ® [9] | 20 |
| Linalol | 40 |
| Mandarine sfuma essential oil | 5 |
| 10% * Spearmint essential oil | 30 |
| Neroli bigarade essential oil | 130 |
| Orange essential oil | 80 |
| Phenethylol | 9 |
| Petitgrain essential oil | 63 |
| Pipol | 5 |
| Rosemary essential oil | 16 |
| Terpineol | 9 |

13

-continued

| Ingredients | Parts by weight |
|---|---|
| Violet essential oil | 50 |
| 1% * Zestover [10] | 30 |
| Total | 2100 |

* in dipropylene glycol (DIPG)
** in triethanolamine
[1] 8,12-epoxy-13,14,15,16-tetranorlabdane
[2] origin: International Flavors and Fragrances, USA
[3] 5-Allyl-1,2,3-trimethoxybenzene; origin: Calchauvet, Grasse, France
[4] origin: Firmenich SA, Geneva, Switzerland
[5] pentadecenolide; origin: Firmenich SA, Geneva, Switzerland
[6] Methyl dihydrojasmonate; origin: Firmenich SA, Geneva, Switzerland
[7] Methyl dihydrojasmonate with a high content of cis isomer; origin: Firmenich SA, Geneva, Switzerland
[8] 1-(octahydro-2,3,8,8-tetramethyl-2-naphtalenyl)-1-ethanone; origin: International Flavors and Fragrances, USA
[9] 3-Hexenyl methyl carbonate; origin: International Flavors and Fragrances, USA
[10] 9-decen-1-ol; origin: International Flavors and Fragrances, USA In a general way, a microemulsion according to the invention was obtained, in a first step, by mixing together, in a beaker, de-ionized water and the surfactants, and the solubilizing-aid ingredient. The mixture was gently stirred at room temperature for a few minutes by means of a common mixing device, such as magnetic stirring device. Optionally, during the stirring the mixture may be protected by a nitrogen blanket. In the second step, the fragrance was added under stirring over the above water solution. The microemulsion was formed in few minutes. Usually a clear product was obtained in less than 10 minutes, sometimes even instantly. Following this general procedure, it was obtained a microemulsion according to Table 1 and 2, and having a oil/surfactant system ratio of 1.71:

TABLE 1 formulation of the microemulsion

| Ingredient | Parts by weight | |
|---|---|---|
| Perfume | 15.18 | |
| Surfactant system: | 8.89 | |
| PEO (20) Sorbitan monooleate | | 2.08 |
| PEO (20) Sorbitan monolaurate | | 0.64 |
| Solubilisant LRI [1] | | 1.64 |
| Sodium Dioctyl Sulfosuccinate | | 3.89 |
| Sodium Dodecylsulfate | | 0.64 |
| Solubilizing-aid ingredient: | 0.98 | |
| Sodium Benzoate | | 0.40 |
| Ajidew NL-50 [1] | | 0.33 |
| Sodium L-lactate | | 0.25 |
| Optional ingredient: | 0.37 | |
| Glydant Plus [3] | | 0.37 |
| De-ionized water | 74.58 | |
| Total | 100.00 | |

[1] 89.7% Aqueous Blend of non-ionic surfactants from LCW
[2] Sodium Pirrolydone Carboxylic Acid 50% aqueous solution from Ajinimoto Inc.
[3] 87% Aqueous solution, origin: Lonza

TABLE 2 physical properties of the microemulsion described in table 1

Clarity [1]

| T = 25° C. | 48.4 NTU (oil droplet size: 28.3 nm) |
|---|---|
| T = 0-2° C. | 49.5 NTU (oil droplet size: 29.8 nm) |
| Surface tension (mN/m) | 26.44 ± 0.05 |

14

TABLE 2-continued physical properties of the microemulsion described in table 1

| Temperature Stability | from 0° C. to 57° C. |
|---|---|
| Viscosity (25° C.) [2] | 7.98 cPs |

[1] NTU is Nephelometric Turbidity Unit, measured on a Turbidimeter VWR Model 66120-200, with a tungsten lamp and 2 photo voltaic cells centered at 90° to the incident light, response between 400 and 600 nm.
[2] Measured with a Brookfield Viscometer with spindle YULA-15 at 30 rpm

Example 2

Preparation of Perfume-in Water Microemulsion According to the Invention

Following the same procedure as described in Example 1, it was obtained a microemulsion according to Table 3 and 4, and having an oil/surfactant system ratio of 1.09:

TABLE 3 formulation of the microemulsion

| Ingredient | Parts by weight | |
|---|---|---|
| Perfume [2] | 10.31 | |
| Surfactant system: | 9.46 | |
| PEO (20) Sorbitan monooleate | | 2.20 |
| PEO (20) Sorbitan monolaurate | | 0.69 |
| Solubilisant LRI [1] | | 1.75 |
| Sodium Dioctyl Sulfosuccinate | | 4.13 |
| Sodium Dodecylsulfate | | 0.69 |
| Solubilizing-aid ingredient: | 0.67 | |
| Sodium Benzoate | | 0.40 |
| Ajidew NL-50 [1] | | 0.27 |
| Optional ingredient: | 0.34 | |
| Glydant Plus [1] | | 0.34 |
| De-ionized water | 79.22 | |
| Total | 100.00 | |

[1] as in Example 1
[2] as in Example 1

TABLE 4 physical properties of the microemulsion described in Table 3

Clarity [1]

| T = 25° C. | 14.0 NTU (oil droplet size: 15.9 nm) |
|---|---|
| T = 0-2° C. | 14.2 NTU (oil droplet size: 18.0 nm) |
| Surface tension (mN/m) | 26.66 ± 0.05 |
| Temperature Stability | from 0° C. to 70° C. |
| Viscosity (25° C.) [2] | 4.50 cPs |

[1] as in Example 1

Example 3

Preparation of Perfume in Water Microemulsion According to the Invention

Using the perfume described in Example 1 and following the general procedure there-described, a microemulsion according to the invention was formed in few minutes. Usually a clear product was obtained in less than 10 minutes, sometimes even instantly.

Alternatively, a mixture of the water and the surfactants was first prepared and the fragrance added thereto. This led to a comparative microemulsion according to the prior art which lacked clarity. Addition of the solubilizing-aid ingredient to this translucid microemulsion made it possible to obtain clear o/w microemulsions according to the invention.

Both the comparative and the invention's microemulsions had the same (perfume/surfactant system ratio), namely 1.75, but the first one was milky, whereas the invention's microemulsion was perfectly clear.

Comparative Microemulsion (According to U.S. Pat. No. 5,374,614)

| Ingredient | Parts by weight | |
|---|---|---|
| Perfume | 30.00 | |
| Surfactant system: | 17.15 | |
| Tergitol 15-S-12 [1] | | 6.15 |
| Tergitol 15-S-9 [1] | | 9.60 |
| SLES (28% aqueous) [2] | | 1.40 |
| De-ionized water | 52.85 | |
| Total | 100.00 | |

[1] EO(12), respectively EO(9), nonyl phenyl ether
[2] Sodium lauryl ether sulphate The comparative microemulsion above-cited was completely translucid, milky and it was impossible to obtain a clear microemulsion thereof.

By addition to the above comparative emulsion of 7.98% w/w of solubilizing-aid ingredient, i.e. AJIDEW® N-50 (sodium pyrrolidone carboxylic acid 50% aqueous solution; origin: Ajinomoto Inc.), a perfectly clear microemulsion was obtained within instants.

The final composition of the microemulsion according to the invention was as follows:

| Ingredient | Parts by weight | |
|---|---|---|
| Perfume | 27.78 | |
| Surfactant system: | 15.89 | |
| Tergitol 15-S-12 [1] | | 5.70 |
| Tergitol 15-S-9 [1] | | 8.89 |
| SLES (28% aqueous) [2] | | 1.30 |
| Solubilizing-aid ingredient: | 3.69 | |
| AJIDEW ® NL-50 [1] | | 3.69 |
| De-ionized water | 52.64 | |
| Total | 100.00 | |

This clear microemulsion displayed a O/(S+SA) ratio of 1.42.

Example 4

Preparation of a Perfume in Water Microemulsion According to the Invention

Following the same procedure as described in Example 3, and using the same perfume oil and the same surfactant system and solubilizing-aid ingredient, microemulsions having an oil/surfactant system ratio of 1.28 were obtained.

Comparative Microemulsion (According to U.S. Pat. No. 5,374,614)

| Ingredient | Parts by weight | |
|---|---|---|
| Perfume | 15.00 | |
| Surfactant system: | 11.75 | |
| Tergitol 15-S-12 [1] | | 4.90 |
| Tergitol 15-S-9 [1] | | 6.05 |
| SLES (28% aqueous) [2] | | 0.80 |
| De-ionized water | 73.25 | |
| Total | 100.00 | |

[1] and
[2] as in Example 3

The comparative microemulsion above-cited was completely translucid, milky.

By addition to the above comparative emulsion of 7.74% w/w of solubilizing-aid ingredient, i.e. AJIDEW® N-50 (sodium pyrrolidone carboxylic acid 50% aqueous solution; origin: Ajinomoto Inc.), a perfectly clear microemulsion was obtained within instants.

The composition of the microemulsion according to the invention was as follows:

| Ingredient | Parts by weight | |
|---|---|---|
| Perfume | 13.92 | |
| Surfactant system: | 10.91 | |
| Tergitol 15-S-12 [1] | | 4.55 |
| Tergitol 15-S-9 [1] | | 5.62 |
| SLES (28% aqueous) [2] | | 0.74 |
| Solubilizing-aid ingredient: | 3.59 | |
| AJIDEW ® NL-50 [1] | | 3.59 |
| De-ionized water | 71.58 | |
| Total | 100.00 | |

This clear microemulsion displayed a O/(S+SA) ratio of 0.96.

Example 5

Preparation of Perfume in Water Microemulsion According to the Invention

Following the same procedure as described in Example 3, and using the same perfume oil and the same surfactant system and solubilizing-aid ingredient, microemulsions having a oil/surfactant system ratio of 1.10 were obtained.

Comparative Microemulsion (According to U.S. Pat. No. 5,374,614)

| Ingredient | Parts by weight | |
|---|---|---|
| Perfume | 5.00 | |
| Surfactant system: | 4.55 | |
| Tergitol 15-S-12 [1] | | 1.90 |
| Tergitol 15-S-9 [1] | | 2.35 |
| SLES (28% aqueous) [2] | | 0.30 |
| De-ionized water | 90.45 | |
| Total | 100.00 | |

[1] and
[2] as in Example 3

The comparative microemulsion above-cited was completely translucid and milky.

By addition to the above comparative emulsion of 7.90% w/w of solubilizing-aid ingredient, i.e. AJIDEW® N-50 (sodium pyrrolidone carboxylic acid 50% aqueous solution; origin: Ajinomoto Inc.), a perfectly clear microemulsion was obtained within instants.

The composition of the microemulsion according to the invention was as follows:

| Ingredient | Parts by weight | |
|---|---|---|
| Perfume | 4.63 | |
| Surfactant system: | 4.22 | |
| Tergitol 15-S-12 [1] | | 1.76 |
| Tergitol 15-S-9 [1] | | 2.18 |
| SLES (28% aqueous) [2] | | 0.28 |
| Solubilizing-aid ingredient: | 3.66 | |
| AJIDEW ® NL-50 [1] | | 3.66 |
| De-ionized water | 87.49 | |
| Total | 100.00 | |

This clear microemulsion displayed an O/(S+SA) ratio of 0.59.

Example 6

Preparation of Perfume in Water Microemulsion According to the Invention

Following the same procedure as described in Example 3, and using the same perfume oil and the same surfactant system and solubilizing-aid ingredient, microemulsions having an oil/surfactant system ratio of 1.10 were obtained.

Comparative Microemulsion (According to U.S. Pat. No. 5,374,614)

| Ingredient | Parts by weight | |
|---|---|---|
| Perfume | 2.00 | |
| Surfactant system: | 1.82 | |
| Tergitol 15-S-12 [1] | | 0.76 |
| Tergitol 15-S-9 [1] | | 0.94 |
| SLES (28% aqueous) [2] | | 0.12 |
| De-ionized water | 96.18 | |
| Total | 100.00 | |

[1] and
[2] as in Example 3

The comparative microemulsion above-cited was completely translucid, milky.

By addition to the above comparative emulsion of 4.04% w/w of solubilizing-aid ingredient, i.e. AJIDEW® N-50 (sodium pyrrolidone carboxylic acid 50% aqueous solution; origin: Ajinomoto Inc.), a perfectly clear microemulsion was obtained within instants.

The composition of the microemulsion according to the invention was as follows:

| Ingredient | Parts by weight | |
|---|---|---|
| Perfume | 1.92 | |
| Surfactant system: | 1.75 | |
| Tergitol 15-S-12 [1] | | 0.73 |
| Tergitol 15-S-9 [1] | | 0.90 |
| SLES (28% aqueous) [2] | | 0.12 |
| Solubilizing-aid ingredient: | 1.94 | |
| AJIDEW ® NL-50 [1] | | 1.94 |
| De-ionized water | 94.39 | |
| Total | 100.00 | |

This clear microemulsion displayed an O/(S+SA) ratio of 0.52.

Example 7

Preparation of Perfume in a Concentrate and in a Microemulsion According to the Invention Compositions according to the invention, having an oil/surfactant system ratio of 1.053 were prepared with the following ingredients:

Formulation of the Compositions

| Ingredient | Parts by weight | |
|---|---|---|
| Perfume [5] | 9.95 | |
| Surfactant system: | 9.45 | |
| Brij 98 [1] | | 2.78 |
| LRI Solubilizer [2] | | 1.85 |
| Aerosol OT 100 [3] | | 4.82 |
| Solubilizing-aid ingredient: | 0.78 | |
| AJIDEW ® NL-50 [4] | | 0.78 |
| De-ionized water | 79.82 | |
| Total | 100.00 | |

[1] Secondary alcohol ethoxylated; origin: Uniquema from ICI Group
[2] PPG-26 Buteth-26 and PEG-40 Hydrogenated Castor Oil; origin: LCW Sensient Cosmetic Technologies
[3] Diethylhexyl Sodium Sulfosuccinate; origin: Cytec Industries, Inc., West Paterson, NJ 07424
[4] See Example 3
[5] Floral, spicy perfume; origin: Firmenich SA The solubilized oil concentrate obtained with the perfume, surfactant system and solubilizing-aid ingredient, as well as the clear microemulsion obtained by dilution thereof in the water, displayed an O/(S+SA) of 0.974.

Example 8

Preparation of Perfume in a Concentrate and in a Microemulsion According to the Invention Compositions according to the invention, having an oil/surfactant system ratio of 1.053 were prepared with the following ingredients:

Formulation of the Compositions

| Ingredient | Parts by weight | |
|---|---|---|
| Perfume [5] | 10.04 | |
| Surfactant system: | 9.54 | |
| GLYCOSPERSE ® O-20 [1] | | 2.81 |
| LRI Solubilizer [2] | | 1.87 |
| Aerosol OT 100 [3] | | 4.86 |
| Solubilizing-aid ingredient: | 0.28 | |
| AJIDEW ® NL-50 [4] | | 0.28 |
| De-ionized water | 80.14 | |
| Total | 100.00 | |

[1] POE(20) Sorbitan monooleate; origin: Lonza
[2] See Example 7
[3] See Example 7
[4] See Example 7
[5] See Example 7

The solubilized oil concentrate obtained with the perfume, surfactant system and solubilizing-aid ingredient, as well as the clear microemulsion obtained by dilution thereof in the water, displayed an O/(S+SA) of 1.023.

Example 9

Preparation of Perfume in a Concentrate and in a Microemulsion According to the Invention Compositions according to the invention, having an oil/surfactant system ratio of 1.053 were prepared with the following ingredients:

Formulation of the Compositions

| Ingredient | Parts by weight | |
|---|---|---|
| Perfume [5] | 7.99 | |
| Surfactant system: | 7.59 | |
| Brij 98 [1] | | 2.23 |
| LRI Solubilizer [2] | | 1.49 |
| SDS [3] | | 3.87 |
| Solubilizing-aid ingredient: | 10.45 | |
| AJIDEW ® NL-50 [4] | | 10.45 |
| De-ionized water | 73.97 | |
| Total | 100.00 | |

[1] See Example 7
[2] See Example 7
[3] Cognis Corporation
[4] See Example 7
[5] See Example 7

The solubilized oil concentrate obtained with the perfume, surfactant system and solubilizing-aid ingredient, as well as the clear microemulsion obtained by dilution thereof in the water, displayed an O/(S+SA) of 0.443.

Example 10

Preparation of Perfume in a Concentrate and in a Microemulsion According to the Invention Compositions according to the invention, having an oil/surfactant system ratio of 1.053 were prepared with the following ingredients:

Formulation of the Compositions

| Ingredient | Parts by weight | |
|---|---|---|
| Perfume [5] | 10.06 | |
| Surfactant system: | 9.55 | |
| Brij 98 [1] | | 2.81 |
| LRI Solubilizer [2] | | 1.87 |
| Aerosol OT 100 [3] | | 4.87 |
| Solubilizing-aid ingredient: | 0.398 | |
| Sodium Lactate powder [4] | | 0.398 |
| De-ionized water | 79.99 | |
| Total | 100.00 | |

[1] See Example 7
[2] See Example 7
[3] See Example 7
[4] Aldrich
[5] See Example 7

The solubilized oil concentrate obtained with the perfume, surfactant system and solubilizing-aid ingredient, as well as the clear microemulsion obtained by dilution thereof in the water, displayed an O/(S+SA) of 1.011.

Example 11

Preparation of Perfume in a Concentrate and in a Microemulsion According to the Invention Compositions according to the invention, having an oil/surfactant system ratio of 1.080 were prepared with the following ingredients:

Formulation of the Compositions

| Ingredient | Parts by weight | |
|---|---|---|
| Perfume [5] | 9.87 | |
| Surfactant system: | 9.14 | |
| Brij 98 [1] | | 2.69 |
| LRI Solubilizer [2] | | 1.79 |
| SDBS [3] | | 4.66 |
| Solubilizing-aid ingredient: | 2.36 | |
| AJIDEW ® NL-50 [4] | | 2.36 |
| De-ionized water | 78.63 | |
| Total | 100.00 | |

[1] See Example 7
[2] See Example 7
[3] Aldrich
[4] See Example 7
[5] See example 7

The solubilized oil concentrate obtained with the perfume, surfactant system and solubilizing-aid ingredient, as well as the clear microemulsion obtained by dilution thereof in the water, displayed an O/(S+SA) of 0.858.

Example 12

Preparation of Perfume Concentrate and Microemulsion

A perfume concentrate and the corresponding microemulsion were prepared with the ingredients indicated below in the amounts cited in the Table. The oil/surfactant system ratio was of 1.205.

TABLE 5

| Ingredients | Weight % |
|---|---|
| Deionized water | 43.675 |
| Aerosol OT 100* | 12.45 |
| TWEEN ® 20 [1] | 0.525 |
| GLYCOSPERSE ®O-20* | 6.60 |
| Solubilizer LRI* | 5.325 |
| Glydant [2] | 0.225 |
| Perfume | 30.00 |
| AJIDEW ® N-50* | 1.20 |

*See Example 7
[1] origin: Uniquema
[2] DMDM Hydantoïn; origin: Lonza

The solubilized oil concentrate obtained with the perfume, surfactant system and solubilizing-aid ingredient, as well as the clear microemulsion obtained by dilution thereof in the water, displayed an O/(S+SA) of 1.149.

The perfume used was prepared by admixture of the following ingredients, in the proportions indicated.

TABLE 6

| Ingredient | Weight % |
|---|---|
| Alpha-Terpinene | 0.11 |
| Alpha-Terpineol | 0.01 |
| Acid C 8 redist | 0.01 |
| Aldehyde C 10 | 0.03 |
| Aldehyde C 11 Lique | 0.01 |
| Aldehyde C 12 | 0.06 |
| Aldehyde C 8 | 0.02 |
| Aldehyde C 9 | 0.03 |
| Alpha-Terpineol | 0.28 |
| Farnesol [1] | 0.38 |
| Benzyl Benzoate | 0.01 |
| Benzyl Formate | 0.01 |
| Bisabolene | 0.08 |
| Borneol Crist | 0.02 |
| Camphene Redist | 0.03 |
| Camphor | 0.08 |
| Caryophyllene | 0.11 |
| CETALOX ® [1] | 0.24 |
| Citral | 0.80 |
| Citronellal CP | 0.02 |
| Citronellol BJ | 0.14 |
| Citronellyl Acetate | 0.14 |
| CITRONOVA ® Orange Terpenes [1] | 0.22 |
| Clary Sage Essential Oil | 0.01 |
| Copahu Essential Oil | 0.13 |
| Decyl Acetate | 0.01 |
| Dihydromyrcenol | 2.86 |
| Dipropylene Glycol | 9.94 |
| Diethylene glycol mono ethyl ether | 0.90 |
| Methyl Anthranilate | 0.78 |
| Elemi Essential Oil | 0.10 |
| Ethyl Acetate | 0.01 |
| Ethyl Citrate | 0.01 |
| Ethyl Linalol | 3.14 |
| Eucalyptol | 0.10 |
| Foliaver [1] | 0.14 |
| Geraniol | 0.44 |
| Geranyl Acetate | 0.84 |
| Geranyl Acetone | 0.01 |
| Germotritine | 0.09 |
| HABANOLIDE ® [1] | 3.10 |
| HEDIONE ® [1] | 10.24 |
| HEDIONE ® HC [1] | 3.43 |
| Indol | 0.07 |
| Iso E Super | 4.05 |
| Lavandin Grosso | 1.24 |
| Lemon Terpenes | 0.76 |
| LIFFAROME ® [2] | 0.01 |
| LILIAL ® | 0.02 |
| Limonene | 13.67 |
| Linalol | 6.80 |

TABLE 6-continued

| Ingredient | Weight % |
|---|---|
| Linalyl Acetate | 18.23 |
| Linalyl Oxide | 0.01 |
| Mandarine Sfuma Essential Oil | 0.24 |
| Methylheptenone | 0.02 |
| Myrcene | 0.28 |
| Mixture of all cis isomers of 9,12-octadecadienoic acid and 9,12,15-octadecatrienoic acid | 0.01 |
| Methyl 9-octadecenoate | 0.04 |
| Nerol BJ | 0.09 |
| Neryl Acetate | 0.32 |
| Ocimene | 0.28 |
| Octyl Acetate | 0.01 |
| Palmitic Acid | 0.02 |
| Paracymene | 0.10 |
| Perillyl alcohol [1] | 0.01 |
| Petitgrain Essential oil | 2.10 |
| Phenethylol | 0.43 |
| Phenylethyl Acetate | 0.01 |
| Pinene | 2.45 |
| Pipol Dist | 0.03 |
| Portugal Florida Essential Oil | 3.81 |
| Rosemary Essential Oil | 0.38 |
| Spearmint Essential Oil | 0.14 |
| Terpenyl Acetate | 0.01 |
| Terpinene G Glidden | 1.25 |
| Terpineol | 0.51 |
| Terpinolene | 0.34 |
| Triethanolamine | 0.51 |
| ☐-ionone [1] | 2.38 |
| Diepoxy-15,16-di-norlabdane [1] | 0.10 |
| Terpinenol | 0.04 |
| Zestover | 0.01 |

[1] origin: Firmenich SA

Example 13

Preparation of Perfume Concentrate and Microemulsion

A perfume concentrate and the corresponding micromulsion were prepared with the ingredients indicated below in the amounts cited in the Table. The oil/surfactant system ratio was of 1.265.

TABLE 7

| Ingredients | Weight % |
|---|---|
| Deionized water | 80.06 |
| Aerosol OT 100* | 2.00 |
| TWEEN ® 20 [1] | 0.175 |
| GLYCOSPERSE ®O-20* | 2.20 |
| Solubilizer LRI* | 3.53 |
| Glydant [1] | 0.0338 |
| Perfume | 10.00 |
| AJIDEW ® N-50* | 2.00 |

*See Example 7
[1] See Example 12

The solubilized oil concentrate obtained with the perfume, surfactant system and solubilizing-aid ingredient, as well as the clear microemulsion obtained by dilution thereof in the water, displayed an O/(S+SA) of 1.01.

The perfume used was prepared by admixture of the following main ingredients, in the proportions indicated.

TABLE 8

| Ingredient | Weight % |
| --- | --- |
| Abalyn | 0.38 |
| Aldehyde C 10 | 0.01 |
| Aldehyde C 8 | 0.01 |
| Aldehyde C 9 | 0.01 |
| Ambrettolide | 0.07 |
| Anozol | 0.04 |
| Astrotone | 1.97 |
| B H T | 0.09 |
| Farnesol [1] | 0.05 |
| Benzyl Acetate | 1.64 |
| Benzyl Salicylate | 2.63 |
| Beta Ionone | 3.62 |
| Bisabolene HLR | 0.03 |
| Caryolan | 0.01 |
| Caryophyllene | 0.06 |
| CETALOX ® [1] | 0.20 |
| Citral | 0.33 |
| Citronellal | 0.01 |
| Citronellol | 1.57 |
| Citronellyl Acetate | 0.27 |
| Citronellyl Formate | 0.01 |
| Citronellyl Propionate | 0.01 |
| CITRONOVA ® Orange Terpenes [1] | 0.16 |
| Clary Sage Essential Oil | 0.01 |
| Copahu Essential Oil Dist | 0.09 |
| Damascenone | 0.13 |
| Decal | 0.13 |
| Dihydromyrcenol | 2.89 |
| Dimethyloctanol | 0.01 |
| Dipropylene Glycol | 1.94 |
| Diethylene glycol mono ethyl ether | 0.39 |
| Ethyl Acetate | 0.01 |
| Ethyl Citrate | 0.02 |
| Ethyl Linalol | 4.74 |
| 7-Methyl-2H,4H-1,5-Benzodioxepin-3-one [1] | 0.07 |
| 3-(Ethylphenyl)-2,2-dimethylpropanal [1] | 0.33 |
| Foliaver [1] | 1.12 |
| Fructone | 0.66 |
| Gamma Damascone [1] | 0.03 |
| Geraniol | 0.12 |
| Geraniol Formiate | 0.02 |
| Geranium Essential Oil | 0.01 |
| Geranyl Acetate | 0.13 |
| Germotritine | 0.03 |
| Grapefruit Essential Oil | 0.66 |
| HABANOLIDE ® [1] | 7.37 |
| HEDIONE ® HC [1] | 6.25 |
| Heliopropanal | 2.66 |
| Hexyl Salicylate | 0.10 |
| Hydroxycitronellol | 0.28 |
| Indol | 0.24 |
| Iso E Super | 2.50 |
| Isopropyl Myristate | 0.12 |
| Isospirene | 0.01 |
| Lavandin Grosso | 0.26 |
| Lemon Terpenes | 0.28 |
| Levocitrol | 0.34 |
| LIFFAROME ® | 0.01 |
| LILIAL ® | 6.91 |
| Limonene Dist | 5.44 |
| Linalol BJ | 1.68 |
| Lynalyl Acetate | 3.00 |
| LYRAL ® | 2.83 |
| Mandarine Sfuma Essential Oil | 1.78 |
| Melonal | 0.02 |
| Menthone | 0.01 |
| Methylheptenone | 0.01 |
| Myrcene | 0.06 |
| Methyl 9-octadecenoate | 0.03 |
| HEDIONE ® [1] | 19.13 |
| NEOBUTENONE ® [1] | 0.01 |
| Nerol BJ | 0.01 |
| Neryl Acetate | 0.12 |
| Octyl Acetate | 0.01 |
| Oxane | 0.01 |
| Palmitic Acid | 0.01 |
| Paracymene | 0.04 |

TABLE 8-continued

| Ingredient | Weight % |
| --- | --- |
| Pepper Essential Oil | 0.01 |
| Perillyl alcohol [1] | 0.01 |
| Phenethylol | 0.77 |
| Phenylacetic Aldehyde | 0.07 |
| Phenylethyl Acetate | 0.02 |
| Phenylhexanol | 0.33 |
| Pinene | 1.03 |
| Pipol Acetate | 0.46 |
| Pipol Dist | 0.13 |
| Pipol Salicylate | 2.63 |
| Portugal Floride ARR | 3.29 |
| RHUBOFIX ® [1] | 0.01 |
| 9-Decen-1-ol [1] | 0.03 |
| Rose oxide | 0.01 |
| Spearmint Essential Oil | 0.13 |
| Styrallyl Acetate | 1.53 |
| Terpinene Alpha | 0.05 |
| Terpinene G Glidden | 0.59 |
| Terpineol Super | 0.02 |
| Terpinolene | 0.16 |
| Tetronic | 0.13 |
| Triethanolamine | 0.07 |
| Veloutone [1] | 0.01 |
| Terpinenol | 0.01 |
| Zestover | 0.16 |

[1] origin: Firmenich SA

Example 14

Preparation of Perfumed Compositions Containing UV Light Absorbers and Sun Screens Compositions having sun screen and UV absorbing properties, in concentrate and clear microemulsion form, were prepared by admixture of the ingredients indicated below in the appropriate amounts to obtain, in the clear microemulsion form, the relative percentages in weight indicated in the table.

TABLE 9

| Ingredients | Compositions (weight %) | |
| --- | --- | --- |
|  | A | B |
| Deionized water | 78.925 | 80.075 |
| Aerosol OT 100* | 4.15 | 4.15 |
| TWEEN ® 20 [1] | 0.175 | 0.175 |
| GLYCOSPERSE ®O-20* | 2.2 | 2.2 |
| Solubilizer LRI* | 1.775 | 1.775 |
| Glydant [2] | 0.075 | 0.075 |
| Perfume | 10 | 10 |
| Parsol MCX [4] | 2 |  |
| AJIDEW ® N-50* | 0.7 |  |
| Uvinul A Plus [3] |  | 1 |
| Sodium Lactate 60 Syrup [5] |  | 0.55 |

*See Example 7
**See Example 8
[1] POE(20)Sorbitan monolaurate; origin: Uniquema
[2] DMDM Hydantoïn; origin: Lonza
[3] Diethylamino Hydroxybenzoyl Hexyl Benzoate; origin: BASF
[4] Ethylhexyl Methoxycinnamate; origin: DSM Nutritional Products The surfactant system formed of the Aerosol OT 100, other surfactant products and the LRI solubilizer was mixed together with the solubilizing-aid agent AJIDEW® N-50 (A) or the Sodium Lactate syrup (B), to form an oil solubilizing agent according to the invention. The latter was then used to prepare a perfume concentrate, by addition of the perfume thereto. The preservative and UV absorber agents, respectively the Glydant and Uvinul or Parsol products, can either be added to the oil solubilizing system, or to the final oil concentrate.

Dilution of the oil concentrate in the water provided the clear microemulsion having UV absorbing and sun-screening properties.

The perfume used was prepared by admixture of the ingredients indicated in the table herebelow, used in the cited weight proportions.

TABLE 10

Perfume composition

| Fragrance ingredients | Parts by weight |
|---|---|
| Vert de lilas [2] | 10 |
| Hydroxycitronellal | 10 |
| Heliotropine Ord | 10 |
| Coumarine | 10 |
| Ethyl vanilline | 10 |
| Phenylhexanol | 10 |
| Heliopropanal | 10 |
| Diethyl 1,4-cyclohexane dicarboxylate [1] | 10 |
| HEDIONE ® [1] | 10 |
| ROMANDOLIDE ® [1] | 10 |
| Muscenone delta [1] | 10 |
| Ambrettolide | 20 |
| Total | 130 |

[1] origin: Firmenich SA
[2] origin: Givaudan

The compositions obtained as described above showed a perfume/surfactant system ratio of 1.2 and a perfume/solubilizing system (i.e. O/(S+SA)) ratio of 1.11 (A), respectively 1.13 (B).

Example 15

Preparation of Perfumed Compositions Containing Vitamin/Antioxidant Agents

Compositions carrying vitamin/antioxidant agents, or their precursors, in concentrate and clear microemulsion form, were prepared by admixture of the ingredients indicated below in the appropriate amounts to obtain, in the clear microemulsion form, the relative percentages in weight indicated in the table.

TABLE 11

| Ingredients* | Compositions (weight %) | | |
|---|---|---|---|
| | A | B | C |
| Deionized water | 80.675 | 80.525 | 79.825 |
| Aerosol OT 100 | 4.15 | 4.15 | 4.15 |
| TWEEN ® 20 | 0.175 | 0.175 | 0.175 |
| GLYCOSPERSE ®O-20 | 2.2 | 2.2 | 2.2 |
| Solubilizer LRI | 1.775 | 1.775 | 1.775 |
| Glydant | 0.075 | 0.075 | 0.075 |
| Perfume | 10 | 10 | 10 |
| Ascorbic acid | 0.5 | 1 | |
| dl-a-Tocopheryl Acetate | | 0.5 | |
| D-Panthenol 75L | | | 1 |
| Sodium Lactate 60 Syrup | 0.45 | 0.6 | |
| AJIDEW ® N-50 | | | 0.8 |

*with the exception of the three vitamin components indicated, the nature of all the ingredients has been indicated in the preceding Example.

The surfactant system formed of the Aerosol OT 100, other surfactant products and the LRI solubilizer was mixed together with the solubilizing-aid agent AJIDEW® N-50 (C) or the Sodium Lactate syrup (A and B), to form an oil solubilizing agent according to the invention. The latter was then used to prepare a perfume concentrate, by addition of the perfume thereto. The vitamin/antioxidant ingredients can either be added to the oil solubilizing system, or to the final oil concentrate.

Dilution of the oil concentrate in the water provided the clear microemulsions carrying vitamin/antioxidant agents beneficial for body care.

The compositions thus obtained showed a perfume/surfactant system ratio of 1.2 and a perfume/solubilizing system (i.e. O/(S+SA)) ratio of 1.142 (A), respectively 1.124 (B) and 1.099 (C).

Example 16

Preparation of Perfumed Compositions Containing Deodorant Ingredients

Compositions carrying deodorizing agents, in concentrate and clear microemulsion form, were prepared by admixture of the ingredients indicated below in the appropriate amounts to obtain, in the clear microemulsion form, the relative percentages in weight indicated in the table.

TABLE 12

| Ingredients* | Compositions (weight %) | |
|---|---|---|
| | A | B |
| Deionized water | 81.225 | 81.075 |
| Aerosol OT 100 | 4.15 | 4.15 |
| TWEEN ®20 | 0.175 | 0.175 |
| GLYCOSPERSE ®O-20 | 2.2 | 2.2 |
| Solubilizer LRI | 1.775 | 1.775 |
| Glydant | 0.075 | 0.075 |
| Perfume | 10 | 10 |
| Sensiva SC50 [1] | 0.2 | |
| AJIDEW ® N-50 | 0.2 | |
| Irgasan DP300 [2] | | 0.25 |
| Sodium Benzoate | | 0.3 |

*with the exception of the deodorant ingredients indicated, the nature of all the ingredients has been indicated in Example 15
[1] Ethylhexyl Glycerin; origin: Seppic
[2] TRICLOSAN ®; origin: Ciba Specialty Chemicals The surfactant system formed of the Aerosol OT 100, other surfactant products and the LRI solubilizer was mixed together with the solubilizing-aid agent AJIDEW® N-50 (A) or the sodium benzoate (B), to form an oil solubilizing agent according to the invention. The latter was then used to prepare a perfume concentrate, by addition of the perfume thereto. The vitamin/antioxidant ingredients can either be added to the oil solubilizing system, or to the final oil concentrate.

Dilution of the oil concentrate in the water provided the clear microemulsions carrying deodorant agents.

The compositions thus obtained showed a perfume/surfactant system ratio of 1.2 and a perfume/solubilizing system (i.e. O/(S+SA)) ratio of 1.177 (A), respectively 1.163 (B).

Example 17

Preparation of Perfumed Compositions Containing Skin Conditioning Agents

Compositions carrying skin conditioning agents, in concentrate and clear microemulsion form, were prepared by admixture of the ingredients indicated below in the appropriate amounts to obtain, in the clear microemulsion form, the relative percentages in weight indicated in the table.

TABLE 13

| Ingredients* | Compositions (weight %) | | | |
|---|---|---|---|---|
| | A | B | C | D |
| Deionized water | 80.675 | 80.275 | 80.175 | 79.425 |
| Aerosol OT 100 | 4.15 | 4.15 | 4.15 | 4.15 |
| TWEEN ® 20 | 0.175 | 0.175 | 0.175 | 0.175 |
| GLYCOSPERSE ®O-20 | 2.2 | 2.2 | 2.2 | 2.2 |
| Solubilizer LRI | 1.775 | 1.775 | 1.775 | 1.775 |
| Glydant | 0.075 | 0.075 | 0.075 | 0.075 |
| Perfume | 10 | 10 | 10 | 10 |
| Urea | 0.5 | | | |
| Sodium Lactate 60 Syrup | 0.45 | | 0.3 | |
| Glucam E-20 [1] | | | | |
| Sodium Benzoate | | 0.35 | | 0.2 |
| Aquaxyll [2] | | 1.15 | | |
| Dow Corning 345 Fluid [3] | | | 2 | |

*with the exception of skin conditioning ingredients indicated, the nature of all the ingredients has been indicated in previous examples
[1] Methyl Gluceth-20; origin: Noveon
[2] (Xylitylglucoside and Anhydroxylitol and Xylitol; origin: Seppic
[3] Cyclopentasiloxane and Cyclohexasiloxane; origin: Dow Corning The surfactant system formed of the Aerosol OT 100, other surfactant products and the LRI solubilizer was mixed together with the solubilizing-aid agent sodium benzoate(A and C) or the Sodium Lactate Syrup (B and D), to form an oil solubilizing agent according to the invention. The latter was then used to prepare a perfume concentrate, by addition of the perfume thereto. The skin conditioning ingredients can either be added to the oil solubilizing system, or to the final oil concentrate.

Dilution of the oil concentrate in the water provided the clear microemulsions carrying skin conditioning agents.

The compositions thus obtained showed a perfume/surfactant system ratio of 1.2 and a perfume/solubilizing system (i.e. O/(S+SA)) ratio of respectively 1.143 (A), 1.156 (B), 1.163 (C) and 1.177 (D).

Example 18

Preparation of a Perfumed Composition Containing Skin Conditioning Agent/Anti-Irritant Agent A composition having a floral odor character and carrying skin conditioning agent/anti-irritant agent, in concentrate and clear microemulsion form, was prepared by admixture of the ingredients indicated below in the appropriate amounts to obtain, in the clear microemulsion form, the relative percentages in weight indicated in the table.

TABLE 14

| Ingredients* | Weight % |
|---|---|
| Deionized water | 80.175 |
| Aerosol OT 100 | 5.87 |
| TWEEN ® 20 | 0.25 |
| GLYCOSPERSE ®O-20 | 3.14 |
| Solubilizer LRI | 2.23 |
| Glydant | 0.18 |
| Floral Perfume | 15 |
| Bacocalmine [1] | 1.8 |
| AJIDEW ® N-50 | 0.18 |

*with the exception of skin conditioning agent/anti-irritant agent indicated, the nature of all the ingredients has been indicated in previous examples
[1] PEG-8 and *Bacopa Monniera* Extract and water(aqua) and hydroxyethylcellulose; origin: Sederma from Croda The surfactant system formed of the Aerosol OT 100, other surfactant products and the LRI solubilizer was mixed together with the solubilizing-aid agent, to form an oil solubilizing agent according to the invention. The latter was then used to prepare a perfume concentrate, by addition of the perfume thereto. The skin conditioning agent/anti-irritant agent can either be added to the oil solubilizing system, or to the final oil concentrate.

Dilution of the oil concentrate in the water provided the clear microemulsion carrying the skin conditioning agent/anti-irritant agent.

The compositions thus obtained showed a perfume/surfactant system ratio of 1.31 and a perfume/solubilizing system (i.e. O/(S+SA)) ratio of respectively 1.285.

Example 19

Preparation of Perfume in Water Microemulsion According to the Invention

Following the same procedure as described in Example 3, and using the same perfume oil but a different surfactant system and solubilizing-aid ingredient, microemulsions according to the invention, having an oil/surfactant system ratio of 1.71 were obtained.

Formulation of the Microemulsion

| Ingredient | Parts by weight | |
|---|---|---|
| Perfume [1] | 15.18 | |
| Surfactant system: | 8.89 | |
| PEO (20) Sorbitan monooleate | | 2.08 |
| PEO (20) Sorbitan monolaurate | | 0.64 |
| Solubilizant LRI [1] | | 1.64 |
| Sodium Dioctyl Sulfosuccinate | | 3.89 |
| Sodium Dodecylsulfate | | 0.64 |
| Solubilizing-aid ingredient: | 0.98 | |
| Sodium Benzoate | | 0.40 |
| AJIDEW ® NL-50 [1] | | 0.33 |
| Sodium L-lactate | | 0.25 |
| Optional ingredient: | 0.37 | |
| Glydant | | 0.37 |
| De-ionized water | 74.58 | |
| Total | 100.00 | |

[1] as in Example 3

The clear microemulsion displayed an O/(S+SA) of 1.54.

Example 20

Preparation of Perfume in Water Microemulsion According to the Invention

Following the same procedure as described in Example 3, a clear microemulsion as described below, having an oil/surfactant system ratio of 1.09, was obtained.

Formulation of the Microemulsion

| Ingredient | Parts by weight | |
|---|---|---|
| Perfume [2] | 10.31 | |
| Surfactant system: | 9.46 | |
| PEO (20) Sorbitan monooleate | | 2.20 |
| PEO (20) Sorbitan monolaurate | | 0.69 |
| Solubilizant LRI [1] | | 1.75 |
| Sodium Dioctyl Sulfosuccinate | | 4.13 |
| Sodium Dodecylsulfate | | 0.69 |
| Solubilizing-aid ingredient: | 0.67 | |

-continued

| Ingredient | Parts by weight |
|---|---|
| Sodium Benzoate | 0.40 |
| AJIDEW ® NL-50 [1] | 0.27 |
| Optional ingredient: | 0.34 |
| Glydant | 0.34 |
| De-ionized water | 79.22 |
| Total | 100.00 |

[1] as in Example 7
[2] as in Example 3

The clear microemulsion thus obtained displayed an O/(S+SA) ratio of 1.02.

To the extent necessary, the entire content of prior application Ser. Nos. 11/689,635 and 11/245,704 are expressly incorporated herein by reference.

What is claimed is:

1. An oil containing composition in the form of a clear microemulsion comprising:
    A) from 0.01 to 80% w/w of an oil;
    B) a surfactant system (S) of one or more surfactants;
    C) a solubilizing-aid ingredient (SA) comprising a pyrrolidone carboxylic acid sodium salt;
    D) optionally water;
        wherein the ratio between the amount of oil (O) and the total amount of surfactant system (S) plus solubilizing-aid (SA) ingredient is comprised between 0.1 and 5.

2. The composition according to claim 1, in the form of a clear microemulsion comprising at least 10% by weight of water.

3. The composition according to claim 2, comprising a perfume in an amount of up to 30% weight, relative to the weight of the composition.

4. The composition according to claim 1, wherein the surfactant system (S) comprises one or more anionic surfactants, and one or more non-ionic surfactants or mixtures of one or more anionic surfactants one or more non-ionic surfactants, in an amount such that the concentration ratio of oil/surfactant is comprised between 1 and 3.

5. The composition according to claim 4, wherein the surfactants system (S) comprises one or more anionic surfactants and one or more non-ionic surfactants with the amount of anionic surfactant or surfactants being at least 50% by weight of the total weight of the surfactant system.

6. The composition according to claim 4, wherein the surfactant system (S) comprises one or more anionic surfactants and one or more non-ionic surfactants with the amount of non-ionic surfactant or surfactants being at least 50% by weight of the total weight of surfactant system.

7. The composition according to claim 4, in the form of a clear microemulsion characterized by a surface tension, measured at 25° C., comprised between 20 and 30 mN/m.

8. The composition according to claim 4, wherein the w/w oil/surfactant system ratio (O/S) is comprised between 1.2 and 2 and the ratio O/(S+SA) is comprised between 0.5 and 2.

9. The composition according to claim 4, wherein:
    a) the anionic surfactants are selected from the group consisting of sodium, potassium, ammonium and mono-, di- and tri-ethanolammonium salts of $C_6$-$C_{12}$ dialkyl sulfosuccinic acids, $C_7$-$C_{24}$ alkarylsulfonic acids, $C_6$-$C_{15}$ alkylsulfuric acid, $C_{10}$-$C_{20}$ acyl glutamic acid, and polyethylene glycol/dimethicone sulfosuccinic acids; and
    b) the non-ionic surfactants are selected from the group consisting of ethoxylated and propoxylated ($C_5$-$C_{12}$ alkyl)phenols ethers containing 5 to 20 EO or PO units, polyethylene glycol sorbitol ether containing 3 to 30 EO units, sucrose esters with $C_8$-$C_{20}$ fatty acid, ethoxylated aliphatic $C_6$-$C_{20}$ alcohols containing 2 to 30 EO units, $C_8$-$C_{20}$ polyglyceryl esters, polyethylene glycol and polypropylene glycol block copolymers, ethoxylated glycol ether containing 2 to 30 EO units, and polyethylene glycol mono- and diesters of aliphatic $C_5$-$C_{11}$ carboxylic acids containing 2 to 10 EO units.

10. The composition according to claim 1, wherein the oil is a perfume, a flavor, an antibacterial agent, a nutraceutical ingredient or a supplement, or a cosmetically active agent.

11. The composition according to claim 10, wherein the oil comprises at least 75% to 90% by weight of a perfume, relative to the weight of oil.

12. The composition according to claim 11, wherein the perfume contains from 5% w/w to 99% w/w of terpenes and/or from 5 to 30% w/w of musks.

13. A consumer article comprising a composition according to claim 1.

14. The consumer article according to claim 13, in the form of a textile freshener, an all-purpose cleaner or a hair or skin preparation.

15. The consumer article according to claim 13, in the form of a beverage, a dairy product or a salad cream.

16. A method to confer, enhance, improve or modify the odor properties of a surface such as skin, hair, glass, tiles, textiles, a kitchen or bathroom surface, which method comprises applying to said surface an olfactive effective amount of a composition as defined in claim 1.

17. A method to confer, enhance, improve or modify the odor, flavor, nutritional, texture, antibacterial, malodor counteracting and/or sun-screening properties, or skin-conditioning benefits, of a composition or of an article, which method comprises adding to said composition or article an effective amount of a composition according to claim 1.

18. The composition according to claim 3, wherein the pyrrolidone carboxylic acid sodium salt is present in a mixture with one or more salts selected from the group consisting of sodium benzoate, sodium L-lactate, calcium L-ascorbate, sodium bicarbonate, di-sodium succinate.

19. An oil containing composition in the form of a clear microemulsion comprising:
    A) from 0.01 to 80% w/w of an oil;
    B) a surfactant system (S) comprising one or more anionic surfactants;
    C) a solubilizing-aid ingredient (SA) comprising a pyrrolidone carboxylic acid sodium salt;
    D) optionally water;
        wherein the ratio between the amount of oil (O) and the total amount of surfactant system (S) plus solubilizing-aid (SA) ingredient is comprised between 0.1 and 5.

* * * * *

UNITED STATES PATENT AND TRADEMARK OFFICE
CERTIFICATE OF CORRECTION

| | | |
|---|---|---|
| PATENT NO. | : 7,846,889 B2 | Page 1 of 1 |
| APPLICATION NO. | : 12/643269 | |
| DATED | : December 7, 2010 | |
| INVENTOR(S) | : Vlad et al. | |

It is certified that error appears in the above-identified patent and that said Letters Patent is hereby corrected as shown below:

<u>Column 29</u>
Lines 44-45 (claim 5, lines 1-2), change the first occurrence of "surfactants" to -- surfactant --.

Signed and Sealed this
Twenty-fifth Day of January, 2011

David J. Kappos
*Director of the United States Patent and Trademark Office*